(12) United States Patent
Valliant et al.

(10) Patent No.: US 6,890,513 B2
(45) Date of Patent: May 10, 2005

(54) METAL-CARBORANE COMPLEXES FOR RADIOIMAGING AND RADIOTHERAPY AND METHODS FOR THEIR PREPARATION

(75) Inventors: John F Valliant, Waterdown (CA); Pierre Morel, Hamilton (CA); Paul Schaffer, Hamilton (CA); Oyebola O. Sogbein, Hamilton (CA)

(73) Assignee: McMaster University, Hamilton (CA)

( * ) Notice: Subject to any disclaimer, the term of this patent is extended or adjusted under 35 U.S.C. 154(b) by 221 days.

(21) Appl. No.: 10/153,879

(22) Filed: May 24, 2002

(65) Prior Publication Data

US 2003/0068271 A1 Apr. 10, 2003

Related U.S. Application Data

(60) Provisional application No. 60/293,189, filed on May 25, 2001.

(51) Int. Cl.$^7$ .............................. A61K 51/00; C07F 5/00
(52) U.S. Cl. ........................... 424/1.65; 534/10; 534/14
(58) Field of Search ............................... 424/1.65, 1.69, 424/1.11; 534/10, 14

(56) References Cited

U.S. PATENT DOCUMENTS

| 5,066,479 A | * 11/1991 | Hawthorne | ................. 424/1.53 |
| 6,187,910 B1 | 2/2001 | Kasina | |
| 6,344,178 B1 | * 2/2002 | Alberto et al. | ............. 424/1.65 |

OTHER PUBLICATIONS

Abram, U. et al. Synthesis and Structures of Technetium(I) and Rhenium(I) Tricarbonyl Complexes with Bis(diphenylthiophosphoryl) amide, (M(CO)3[(Ph2PS)2N](CH3CN)) (M=Tc, Re). Polyhedron 1998, pp. 1303–1309, vol. 17, No. 8.

Alberto, R. et al. Reactions with th+e Technetium and Rhenium Carbonyl Complexes (NEt4)2[MX3(CO)3]. Synthesis and Structure of [Tc(CN–But)3(CO)3](NO3) and (NEt4)[Tc2(µ–SCH2CH2OH)3(CO)6]. Polyhedron, 1996, pp. 1079–1089, vol. 15 No. 7.

Alberto, R. et al. Metal Carbonyl Syntheses XXII. Low Pressure Carbonylation of [MOCl4]– and [MO4]–: The Technetium(I) and Rhenium(I) Complexes [NEt4]2 [MCl3(CO)3]. J. Organomet. Chem. 1995, pp. 119–127, vol. 493.

Alberto, R. et al. First Application of fac–[99mTc(OH2)3(CO)3]+ in Bioorganometallic Chemistry: Design, Structure, and in Vitro Affinity of a 5–HT1A Receptor Ligand Labelled with 99mTc. J. Am. Chem. Soc. 1999, pp. 6076–6077, vol. 121.

Alberto, R. et al. A Novel Organometallic Aqua Complex of Technetium for the Labelling of Biomolecules: Synthesis of [99mTc(OH2)3(CO)3]+ from [99mTcO4]– in Aqueous Solution and Its Reaction with a Bifunctional Ligand. J. Am. Chem. Soc., 1998, pp. 7987–7988. 120.

Barth, R.F. et al. Determination of Boron in Tissues and Cells Using Direct–Current Plasma Atomic Emission Spectroscopy. Anal. Chem. 1991, pp. 890–893, vol. 63.

Blandford, I. et al. Synthesis and Crystal Structure of the Novel Dianion [Re(CO)3(η5–7–CB10H11)]2–. Reactions with Platina and Palladaphosphine Chlorides. Organometallics 1998, pp. 1402–1411, vol. 17.

Bregadze, V.I. Dicarba–doso–dodecarboranes C2B10H12 and Their Derivatives. Chem. Rev. 1992, pp. 209–233, vol.92.

Cesati III, R.R. et al. One–Pot Formation of Substituted Cyclopentadienyl and Indenyltricarbonyl Rhenium Complexes Through in Situ Generation of Cyclopentadienyl– and Indenyltributylstannanes. J. Am. Chem. Soc. 2001, pp. 4093–4094, vol. 123.

Dilworth, J.R. et al. The Biomedical Chemistry of Technetium and Rhenium. Chem. Soc. Rev. 1998, pp. 43–55, vol. 27.

Ellis, D.D. et al. Studies with the Rhenacarborane Cs[Re(CO)3(η5–7,8–C2B9H11)]: Surprising Reactivity with a Range of Metal Ligand Fragments. Organometallics 1999, pp. 4982–4994, vol. 18.

Hawthorne, M.F. et al. Carbametallic Boron Hydride Derivatives. I. Apparent Analogs of Ferrocene and Ferricinium Ion. J. Am. Chem. Soc. 1965, p. 1818–1819, vol. 87, No. 8.

Hawthorne, M.F. et al. Carbametallic Boron Hydride Derivatives. II. Apparent Analogs of –π.C5H5Mn(CO)3 and Π–C5H5Re(CO)3. J. Am. Chem. Soc. 1985, II. 2496, vol. 87, No. 11.

Hawthorne, M.F. et al. Applications of Radiolabeled Boron Clusters to the Diagnosis and Treatment of Cancer. Chem. Rev. 1999, pp. 3421–3434, vol. 99.

Hawthorne, M.F. et al. Radiometallacarboranes as Tumor Imaging Reagents. J. Am. Chem. Soc. 1990, pp. 5385–5368, vol. 112.

Hawthorne, M.F. et al. p–Dicarbollyl Derivatives of the Transition Metals. Metallocene Analogs. J. Am. Chem. Soc. 1968, pp. 879–896, vol. 90, No. 4.

Imahori, Y. et al. Positron Emission Tomography–based Boron Neutron Capture Therapy Using Boronophenylalanine for High–Grade Gliomas: Part II1. Clin. Cancer Res. 1998, pp. 1833–1841, vol. 4, No. 8.

(Continued)

*Primary Examiner*—Michael G. Hartley
(74) *Attorney, Agent, or Firm*—Bereskin & Parr (57) ABSTRACT

The present invention relates to a new method for the preparation of radiopharmaceuticals based on technetium and rhenium. The method involves the reaction of a salt of the formula $[M(CO)_3(X^m)_3]^{(1+3m)}$, wherein M is selected from a radioisotope of rhenium, technetium and any other radioisotope that binds in a similar fashion, X is any suitable ligand and m is the formal charge for ligand X, with a nido-dicarbollide dianion of the formula $[nido\text{-}(C_2B_9H_{11})]^{2-}$ and functional derivatives thereof. The method has been shown to be applicable to the preparation of radiopharmaceuticals at the tracer level.

20 Claims, 3 Drawing Sheets

Jurisson, S.S. et al. Potential Technetium Small Molecule Radiopharmaceuticals. Chem. Rev. 1999, pp. 2205–2218, vol. 99.

Minutolo, P. A et al. Convenient Three–Component Synthesis of Substituted Cyclopentadienyl Tricarbonyl Rhenium Complexes. J. Am. Chem. Soc. 1998, pp. 4514–4515, vol. 120.

Minutolo, P. et al. Boronic Acids in the Three–Component Synthesis of Carbon–Substituted Cyclopentadienyl Tricarbonyl Rhenium Complexes. J. Am. Chem. Soc. 1998, pp. 13264–13265, vol. 120.

Minutold, P. A et al. Polymer–Supported Phosphazine as a Stable and Practical Reagent in the Three–Component Synthesis of Substituted (Cyclopentadienyl)–tricarbonyl-rhenium Complexes. Angew. Chem. Int. Ed. Engl. 1999, p. 1617–1620, vol. 38, No. 11.

Peymann, T. et al. Dodecamethyl–closo–dodecaborate(2–). Inorg. Chem. 2001, pp. 1291–1294, vol. 40.

Roush, W.R et al. Studies on the Synthesis of Nargenicin A1: Highly Stereoselective Synthesis of the Complete Carbon Framework via the Transannular Diels–Alder Reaction of an 18–Membered Macrolide. J. Am. Chem. Soc. 1996, pp. 7502–7512, vol. 118.

Schibli, R. et al. Structural and 99Tc NMR Investigations of Complexes with fac–[Tc(CO)3]+ Moieties and Macrocyclic Thioethers of Various Ring Sizes: Synthesis and X–ray Structure of the Complexes fac [Tc(9–ane–S3)(CO)3]Br, fac–[Tc2(tosylate)2(18–ane–S8)(CO)6], and fac–[Tc2(20–ane–S6–OH)(CO)6][tosylate]2. Inorg. Chem. 1998, pp. 3509–3516, vol. 37.

Soloway, A.H. et al. The Chemistry of Neutron Capture Therapy. Chem. rev. 1998, pp. 1515–1562, vol. 98.

Stalteri, M.A. et al. Comparison of the Stability of Technetium–Labeled Peptides to Challenge with Cysteine. Bioconj. Chem. 1999, pp. 130–136, vol. 10.

Top. S. A et al. Novel and Mild Metal–Exchange Reaction in the Organometallic Cyclopentadienyl Series. 1,1'–Diaryl 2–Cymantrenyl 1–Butene as an Example. J. Am. Chem. Soc. 2000, pp. 736–737, vol. 122.

Young, D.A.T. et al. Alkylaluminum and Alkylgallium Derivatives of (3)–1,2–B9C2H13. J. Am. Chem. Soc., 1971, pp. 5687–5694, vol. 93, No. 22.

* cited by examiner

METAL-CARBORANE COMPLEXES FOR RADIOIMAGING AND RADIOTHERAPY AND METHODS FOR THEIR PREPARATION

This application claims benefit of priority filing, U.S. Application No. 60/293,189 filed May 25, 2001.

FIELD OF THE INVENTION

The present invention relates to new radiopharmaceuticals, in particular carborane complexes of technetium and rhenium, and new methods for their preparation.

BACKGROUND OF THE INVENTION

The synthesis of low oxidation state technetium (Tc) and rhenium (Re) radiopharmaceuticals has become feasible recently because of the ease with which fac-[M(CO)$_3$X$_3$]$^n$ (M=Tc, Re; X=Cl or Br, n=−2; X=H$_2$O, n=+1) can be prepared at the tracer level,[1] using $^{99m}$Tc (γ, t$_{1/2}$=6.02 h), $^{186}$Re (β−, t$_{1/2}$=91 h) and $^{188}$Re (β−, t$_{1/2}$=17 h), and on a macroscopic scale[2] using $^{99}$Tc (β−, t$_{1/2}$=2.12×10$^5$ yr) and $^{185,187}$Re. Consequently, several publications describing the preparation of technetium(I) and rhenium(I) radiopharmaceuticals have appeared in the literature.[3] These complexes are typically composed of bidentate[4] or tridentate chelates[5] or organometallic ligands.[6]

There has been particular interest lately in preparing substituted η$^5$-cyclopentadienyltricarbonyl rhenium and technetium complexes because of their unique physical and chemical properties compared with Tc(V) and Re(V) coordination complexes, which, at present, are more commonly used to develop new radiopharmaceuticals. The main obstacle to using cyclopentadiene (Cp) as the core of bifunctional radiopharmaceutical ligands has been the lack of a mild and direct method for the synthesis of the metal complexes, which is readily adaptable for use at the tracer level. Top et al.[7] reported an elegant method for preparing rhenium(I) complexes of substituted cyclopentadienes through an exchange reaction with cyclopentadienyltricarbonyl manganese derivatives while Katzenellenbogen's[8] group has reported a one pot procedure for preparing cyclopentadienyltricarbonylrhenium through the in situ generation of Cp-trialkylstannane derivatives. The involvedness of the procedures and, in the latter case, the poor yields of synthesis in concert with the required use of potentially toxic reagents, at present, limit the widespread use of Cp as a bifunctional radionuclide ligand.

The carborane, 7,8-dicarba-nido-undecaborate, when deprotonated, has an open pentagonal face that can form metallocene-type sandwich complexes with analogy to the formally isolobal Cp$^-$ ion.[9] As a result, η$^5$-carborane complexes with a variety of metals have been reported, two of the earliest being [Re(CO)$_3$(η$^5$-7,8-C$_2$B$_9$H$_{11}$)]$^-$ (1, FIG. 1) and [Mn(CO)$_3$(η$^5$-7,8-C$_2$B$_9$H$_{11}$)]$^-$.[10] The original method for the preparation of [Re(CO)$_3$(η$^5$-7,8-C$_2$B$_9$H$_{11}$)]$^-$involved reacting [nido-7,8-(C$_2$B$_9$H$_{11}$)]$^{2-}$, the dicarbollide dianion, with Re(CO)$_5$Br. Ellis et al. reported an improved synthetic procedure starting with [ReBr(CO)$_3$(THF)$_2$] prepared in situ from ReBr(CO)$_5$ under anhydrous conditions.[11] The corresponding reaction with technetium was never reported, which may have been a consequence of radioactivity issues and/or the fact that the synthesis of Tc(CO)$_5$Br is not uncomplicated. Convenient methods for preparing M(CO)$_5$Br (M=$^{99m}$Tc and $^{186,188}$Re) in aqueous solutions at the tracer level suitable for routine radiolabeling experiments do not, at present, exist.

There is a need for new methodologies for the synthesis of radiopharmaceuticals, in particular radiopharmaceuticals of η$^5$-carborane complexes of technetium and rhenium, that are suitable for routine radiolabeling experiments (i.e. can be performed in aqueous solutions at tracer levels).

SUMMARY OF THE INVENTION

η$^5$-Technetium and rhenium carborane π-complexes, including bifunctional derivatives, were prepared in high yield from the reaction of fac-[M(CO)$_3$Br$_3$]$^{2-}$and fac-[M(CO)$_3$(OH$_2$)$_3$]$^{1+}$(M=Re, Tc) with a dicarbollide dianion ([nido-(C$_2$B$_9$H$_{11}$)]$^{2-}$), and functional derivatives thereof. The products, [M(CO)$_3$(η$^5$-C$_2$B$_9$H$_{10}$)]$^-$, and corresponding functional derivatives, which include the first examples of Tc-carborane complexes, where characterized by multi-NMR spectroscopy, X-ray crystallography and mass spectrometry.

The present invention therefore provides a method for preparing metal-carborane complexes comprising reacting a salt of the formula:

$[M(CO)_3(X^m)_3]^{(1+3m)}$, wherein M is selected from a radioisotope of rhenium, technetium and any other radioisotope that binds in a similar fashion, X is any suitable ligand and m is the formal charge for ligand X, with a nido-dicarbollide dianion of the formula [nido-(C$_2$B$_9$H$_{11}$)]$^{2-}$, and functional derivatives thereof. The functional derivatives preferably include nido-dicarbollide dianions in which one or more linker group has been incorporated within the structure. The linker serves to connect the metal-carborane complex with a biological targeting ligand. Alternatively, the biological targeting ligand may have the metal carborane complex incorporated within its structure or directly attached thereto.

The present invention also relates to novel metal-carborane complexes. Therefore there is provided a metal carborane complex comprising the formula [M(CO)$_3$(η$^5$-7,8-C$_2$B$_9$H$_{10}$)]$^-$, wherein M is a radioisotope of technetium; a metal-carborane complex comprising the formula [M(CO)$_3$(η$^5$-7,9-C$_2$B$_9$H$_{10}$)]$^-$, wherein M is selected from a radioisotope of technetium and rhenium, and functional derivatives thereof. The invention also includes a metal-carborane complex having the formula [M(CO)$_3$(η$^5$-7-R-7,8-C$_2$B$_9$H$_{10}$)]$^-$, [M(CO)$_3$(η$^5$-8-R'-7,8-C$_2$B$_9$H$_{10}$)]$^-$ or [M(CO)$_3$(η$^5$-7-R,8-R'-7,8-C$_2$B$_9$H$_{10}$)]$^-$, wherein M is selected from a radioisotope of technetium and rhenium and R and R' are independently selected from (CH$_2$)$_n$CO$_2$H, NH$_2$ and NH—NH$_2$, wherein n is 0–50; and a metal-carborane complex having the formula [M(CO)$_3$(η$^5$-7-R-7,9-C$_2$B$_9$H$_{10}$)]$^-$, [M(CO)$_3$(η$^5$-9-R'-7,9-C$_2$B$_9$H$_{10}$)]$^-$ or [M(CO)$_3$(η$^5$-7-R,9-R'-7,9-C$_2$B$_9$H$_{10}$)]$^-$, wherein M is selected from a radioisotope of technetium and rhenium and R and R' are independently selected from (CH$_2$)$_n$CO$_2$H, NH$_2$ or NH—NH$_2$, wherein n is 0–50.

The invention also includes the use of the metal-carborane complexes prepared using the method of the invention to prepare radiopharmaceuticals. The invention also includes radiopharmaceutical compositions comprising a metal carborane complex prepared using the method of the invention and a pharmaceutically acceptable carrier.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Carboranes, which can be readily derivatized with a range of functional groups, have been used successfully as carriers of a variety of different radionuclides including some radio-metals.[12] This is typified by the report by Hawthorne et al. describing the synthesis of a pyrazole-bridged dicarbollide or "Venus Flytrap" ligand,[13] which was used to prepare bifunctional complexes of $^{57}Co$ ($\eta$, $t_{1/2}$=271d). The synthesis of technetium-carborane complexes have thus far not been reported despite the fact that $^{99m}Tc$ is the most widely used radionuclide in diagnostic medicine.[14] The present inventors have now prepared $\eta^5$-technetium and rhenium carborane $\pi$-complexes, including bifunctional derivatives, in high yield from the reaction of fac-$[M(CO)_3Br_3]^{2-}$ and fac-$[Re(CO)_3(OH_2)_3]^{2+}$ (M=$^{99}Tc$, Re) with a dicarbollide dianion ($[nido-(C_2B_9H_{11})]^{2-}$, and functional derivatives thereof.

Accordingly, the present invention provides a method for preparing metal-carborane complexes comprising reacting a salt of the formula $[M(CO)_3(X^m)_3]^{(1+3m)}$, wherein M is selected from a radioisotope of rhenium, technetium and any other radioisotope that binds in a similar fashion, X is any suitable ligand and m is the formal charge for ligand X, with a nido-dicarbollide dianion of the formula $[nido-(C_2B_9H_{11})]^{2-}$, and functional derivatives thereof.

In embodiments of the present invention, the salts of the formula $[M(CO)_3(X^m)_3]^{(1+3m)}$ include those where M is selected from a radioisotope of rhenium, technetium and any other radioisotope that binds in a similar fashion. A person skilled in the art would be able to determine which radio-isotopes bind in a similar fashion to Tc and Re. Examples include radioisotopes of Rh, Cr, Mo, Mn, Os, Ir and Ru. The ligand "$X^m$" may be any such suitable ligand, including, for example, Cl⁻(m=−1), Br−(m=−1), $PR_3$ (m=0), RCN (m=0), $NO_x^y$ (x=1,2; y=1, −1) and $H_2O$ (m=0). A person skilled in the art would know which ligands are suitable for use in the salts of the formula $[M(CO)_3(X^m)_3]^{(1+3m)}$, based on those known in the art. A suitable ligand will be compatible with the reaction conditions used in the method of the invention. It will be appreciated that one or more of the "CO" ligands many be substituted with any ligand that is isoelectronic and isolobal therewith. Examples of such ligands include NO⁺, $PR_3$, and RCN. The present invention extends to cover the use of salts of the formula $[M(CO)_3(X^m)_3]^{(1+3m)}$ in which one or more of the CO ligands has been substituted with a ligand that is isoelectronic and isolobal therewith. An example of such a complex wherein one CO has been replaced with NO+ is found in Rattat et al. Cancer Biotherapy & Radiopharmaceuticals, 2001, 16(4), 339–343. A person skilled in the art would also understand that the salts of the formula $[M(CO)_3(X^m)_3]^{(1+3m)}$ may require one or more counterions to balance the charge on the complex. Any such counterion compatible with the reaction conditions may be used in the method of the invention.

The salts of the formula $[M(CO)_3(X^m)_3]^{(1+3m)}$ may be prepared using methods known in the art. For example, salts of the formula $[M(CO)_3Br_3]^{2-}$ (M=Re, $^{99}Tc$) may be prepared as described in Alberto et al. 1995.[15] In general these compounds may be prepared, for example, using low temperature reductions of $[NBu_4][MO_4]$ in the presence of CO. The reducing agent may be any suitable reagent, such as a boron hydride, including $BH_3$-THF and $NaBH_4$.

Figure 1:
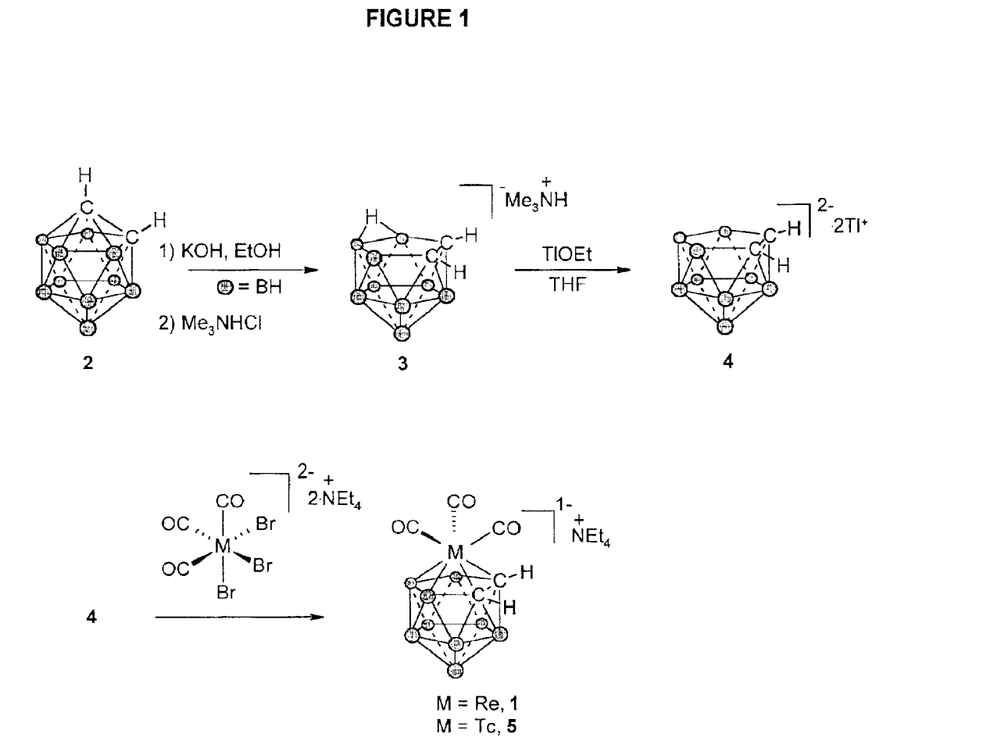
FIG. 1 is a schematic showing the conversion of an ortho-carborane to the corresponding nido-dicarbollide dianion, followed by reaction with a $[M(CO)_3X_3]^{2-}$ salt to provide Tc and Re carborane complexes.

The nido-dicarbolide dianion may be derived from the possible isomers of carborane, for example, ortho- and meta-carborane, which provide the corresponding 7,8- and 7,9-nido-dicarbollide dianions respectively. The nido-dicarbollide dianions may also be used in optically pure form or as a racemic mixture. The invention includes the use of all isomers and mixtures thereof in any proportion The nido-dicarbollide dianions can be prepared using procedures known in the art. For example, from the corresponding ortho- and meta-carboranes by a two step process involving deboronation, to provide the dicarba-nido-undecaborate, $[nido-(C_2B_9H_{12})]^-$, followed by deprotonation. The deboronation reaction may be effected using a base under a variety of conditions.[16,17] For example, ortho-carborane or meta-carborane may be heated to reflux with potassium hydroxide in an alcoholic solvent, such as ethanol. Other bases that can be used include secondary amines, such as pyrolidine, and fluoride. The 7,8-dicarba-nido-undecaborate or 7,9- dicarba-nido-undecaborate product may be isolated as a salt, for example an ammonium salt such as trimethylammonium, or a phosphonium salt such as methyl triphenylphosphonium, using standard procedures. Deprotonation of the dicarba-nido-undecaborates, to yield $[nido-(C_2B_9H_{11})]^{2-}$, may be accomplished using a strong base, such as TlOEt. The conversion of orthocarborane 2 to 7,8-dicarba-nido-undecaborate, trimethylammonium salt, 3, followed by the reaction of 3 with TlOEt to provide the nido-dicarbollide dianion 4, is depicted in FIG. 1 as a representative example.

In order to be useful as a radiopharmaceutical ligand, a means to conjugate the carborane-M(CO)₃ unit to targeting biomolecules must be available. To this end one or more linker moieties may be incorporated into the nido-dicarbollide dianions. Accordingly, the term "functional derivatives" includes carboranes in which a linker group has been attached to one or more of the carbon and/or boron atoms. The one or more linkers may be the same or different. In embodiments of the present invention, the one or more linker groups are attached to the carbon atoms in the carborane. In further embodiments, one linker group is attached to one of the carbon atoms in the carborane. The term "functional derivative" further includes one or more linker groups with a biological targeting molecule attached thereto.

When the metal-carborane complex includes one or more linker groups attached to a biological targeting ligand, the compounds prepared using the method of the invention may be represented as:

wherein M is selected from radioisotopes of Tc, Re and any other radioisotope that binds in a similar fashion (for example $^{105}Rh$), R is a linker group, p is 0–1 and Lig is a ligand having specificity for a biological target. As used herein, the term "linker group" means any functional grouping that allows the metal-carborane complex to be conjugated to a biological target ligand. Generally, the linker group will have a reactive functional group at the end opposed to the metal-carborane complex, to allow reaction with (and therefore conjugation to) a reactive functional grouping on the biological target ligand. The one or more linker groups may be the same or different. The specific linker groups used herein comprise a carboxylic acid which is capable of reacting with, for example, free amino, hydroxy or thiol groups on a biological targeting ligand and a hydrazino group, which is capable of reacting with, for example, a carboxylic acid or other electrophilic group on a biological targeting ligand. Therefore, in embodiments of the present invention, the linker group is selected from $(CH_2)_nCO_2H$, where n is 0–50, $NH_2$ and $NH-NH_2$. In embodiments of the invention, n is 0–10. In further embodiments, n is 0–5.

Examples of biological targeting ligands include, but are not limited to, small molecules having specificity for a specific receptor, immunoproteins, oligopeptides, sugars, cocacin analogues and polypeptides such as epidermal growth factor. The applications of radiolabelled boron clusters to the diagnosis and treatment of cancer has been recently reviewed.[13]

The term "functional derivative" further includes metal carborane complexes that have been incorporated within the structure of a biological targeting ligand. When the metal-carborane complex is incorporated within the structure of a biological targeting ligand, the ligand is preferably a compound having a functional group that is structurally and electronically similar to the carborane moiety. Examples of such functional groups include phenyl and adamantyl groups. An example of such a ligand is the antiestrogen, tamoxifen. The preparation of carborane analogs of tamoxifen is described in inventor Valliant's publication Valliant et al. J. Org. Chem. 2002, 67, 383–387, the contents of which are incorporated herein by reference.

Figure 2:
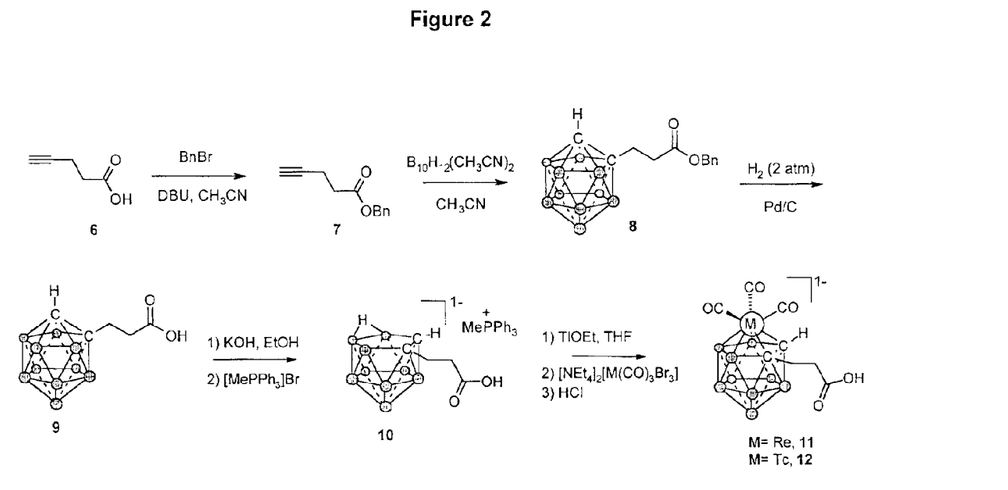
FIG. 2 is a schematic showing the preparation of Tc and Re carborane complexes in which a linker group has been incorporated into the carborane moiety.
Figure 3:
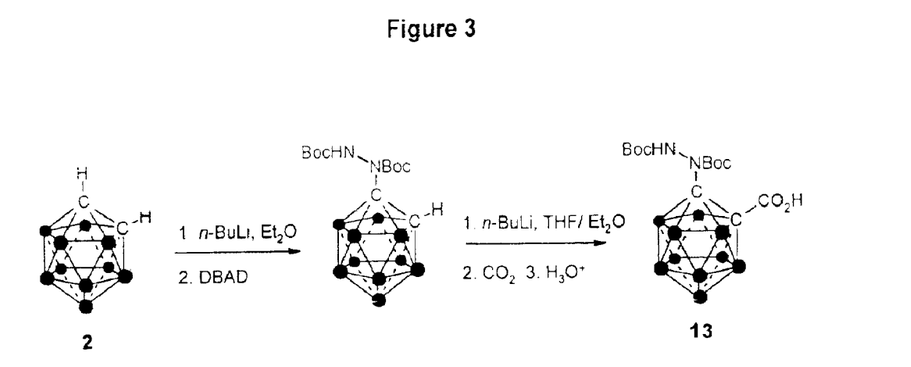
FIG. 3 is a schematic showing the preparation of a bifunctional carborane.

Functionalization of the carborane may be performed before or after the formation of the metal complex using methods known in the art (see for example, references 12 and 13). For example, ortho-carboranes are readily synthesized from the reaction of an appropriately substituted acetylene with various nitrile and sulfide adducts of decaborane $(B_{10}H_{14})$.[18] The linker group may be incorporated into the carborane by judicious choice of the starting acetylene compound. Hydrophilic groups on the acetylenic compounds should be protected in order that the synthetic sequence will produce the desired ortho-carborane. Also, the linker group may be modified using standard procedures at any stage during the preparation of the metal-carborane complex, including modification of the complex itself. As a representative example, the nido-acid 10 (linker=$(CH_2)_2CO_2H$) was prepared (FIG. 2) and its ability to complex rhenium and technetium evaluated. The acid 9, prepared by hydrogenation of the benzyl ester 8, was converted to nido-anion 10, as a mixture of enantiomers, using the aforementioned KOH/EtOH procedure, and the product isolated as the methyl triphenylphosphonium salt (FIG. 2). Alternatively, the carbon and boron centers of the carboranes may be directly functionalized. For example, one or both of the carbon centers may be deprotonated using a strong base such as an alkyl lithium, for example butyllithium, and the resulting anion reacted with any electrophilic reagent. An example of this is shown in FIG. 3 where the ortho-carborane 2 was difunctionalized by first reacting with one equivalent of butyllithium followed by treatment with di-tert-butyl azodicarboxylate. Treatment with a second equivalent of butyl lithium followed by reaction with $CO_2$, provided, after acidification, the hydrazino carborane carboxylic acid 13. The same reaction sequence was successfully performed on the corresponding meta-carborane 14. In general, the B–H vertexes of the carboranes may also be functionalised by electrophilic substitution reactions reminiscent of aromatic hydrocarbon reactions.

The preparation of the metal-carborane complexes may be effected by reacting a nido-dicarbollide dianion with a salt of $[M(CO)_3(X^m)_3]^{(1+3m)}$ in either aqueous or polar organic solvents, such as tetrahydrofuran (THF). The reaction mixture may be warmed and allowed to proceed for a time period of about 1 hour to about 48 hours. The extent of the reaction can be monitored by thin layer chromatography (TLC), therefore a person skilled in the art would be able to determine when the reaction was complete and adjust the reaction time and temperature accordingly. In an embodiment of the invention, the nido-dicarbollide dianion is generated from the corresponding dicarba-nido-undecaborate by treatment with a strong base such as TlOEt or potassium hydroxide (KOH) and a solution of a salt of the formula $[M(CO)_3(X^m)_3]^{(1+3m)}$ is mixed with the nido-dicarbollide dianion directly (i.e. without isolation of the nido-dicarbollide dianion). In further embodiments, the nido-dicarbollide dianion is present in excess amounts. It is also possible to generate the nido-dicarbollide dianion directly from the corresponding ortho-carborane in the presence of a metal complex using a known in situ deboronation reaction (see Hawthorne, M. F. J. Organomet. Chem. 1975, 100, 97–110). This reaction may be used to generate the nido-dicarbollide dianion directly from the ortho-carborane in the presence of the salt of the formula $[M(CO)_3(X^m)_3]^{(1+3m)}$.

As a representative example, the addition of the nido-dicarbollide dianion 4 to a THF solution of $[M(CO)_3Br_3]^{2-}$ is shown in FIG. 1. After gentle reflux overnight the product was isolated by preparative TLC. In the example reported herein, the yield of the technetium-carborane complex 5 was approximately 80% while the Re complex 1 was consistently isolated in nearly quantitative yield. Negative ion electrospray mass spectrometry indicated the presence of the two target compounds each containing the expected isotopic distributions. The ν (CO) absorptions for the Re-carborane complex were 2009 $cm^{-1}$, 1896 $cm^{-1}$ and 1865 $cm^{-1}$, which was identical to that previously reported for 1.[19] Compound 5 exhibited ν (CO) absorbances at 2016 $cm^{-1}$, 1918 $cm^{-1}$, and 1908 $cm^{-1}$ respectively. The B–H stretching frequencies were broad ($ν_{average}$ (1)=2556 $cm^{-1}$, $ν_{average}$ (5)=2523 $cm^{-1}$) and within the expected range for related metallocarboranes including $[Re(CO)_3(\eta^5\text{-}7\text{-}CB_{10}H_{11})]^{2-}$, reported by Blandford et al.[20] The $^{11}B$ NMR of 1 showed peaks ranging from −24.16 to −7.99 ppm and were identical to the shifts reported previously. The $^{11}B$ NMR for 5 was, as expected, similar to that of 1.

The method of the invention was also shown to work with the nido-dicarbollide dianion having a linker group incorporated within its structure. As shown in FIG. 2, a slight excess of compound 10 was treated with two equivalents of TlOEt followed by the addition of the limiting reagent, $[Re(CO)_3Br_3]^{2-}$. The product, 11, isolated by preparative TLC in 99% yield. The Tc analogue 12 was prepared analogously and isolated in 93% yield.

Compounds 11 and 12 were characterized by MS, $^1H$, $^{13}C$ and $^{11}B$ NMR, IR, HPLC and in the case of compound 11 by elemental analysis. All results were in agreement with the proposed structures. The IR of 11 and 12 exhibited B–H stretches at similar frequencies (2524 $cm^{-1}$ and 2529 $cm^{-1}$)

and the $^1$H and $^{13}$C NMR spectra were, as expected, similar. The $^{11}$B NMR for 11 and 12 showed substantial overlap and, due to the loss of symmetry, increased complexity compared to that for compounds 1 and 5. The preparation of compounds 11 and 12 was also effected in aqueous solution (Example 10), confirming the applicability of the method of the invention to the preparation of radiopharmaceuticals at tracer levels. Further confirmation of this was obtained by preparing complexes 5 and 12 at tracer levels (see Example 16).

The stability of the Re and Tc carborane complexes were evaluated using a cysteine challenge experiment.[21] Compound 1, for example, was incubated with a thousand fold excess of cysteine in a 1:1 (v/v) phosphate buffer (pH=7.4)-ethanol mixture at 37° C. over 24 hours. HPLC, FTIR, and electrospray mass spectrometry experiments indicated that the complexes showed no signs of decomposition over the entire duration of the experiment.

Compounds of the Invention

The present invention also relates to novel metal-carborane complexes. Therefore there is provided a metal carborane complex having the formula $[M(CO)_3(\eta^5\text{-}7,8\text{-}C_2B_9H_{10})]^-$ wherein M is a radioisotope of technetium; and a metal-carborane complex having the formulae and $[M(CO)_3(\eta^5\text{-}7,9\text{-}C_2B_9H_{10})]^-$, wherein M is selected from a radioisotope of technetium and rhenium, and functional derivatives thereof.

In specific embodiments of the present invention, the functional derivative has the formula $[M(CO)_3(\eta^5\text{-}7\text{-}R\text{-}7,8\text{-}C_2B_9H_{10})]^-$, $[M(CO)_3(\eta^5\text{-}8\text{-}R'\text{-}7,8\text{-}C_2B_9H_{10})]^-$ or $[M(CO)_3(\eta^5\text{-}7\text{-}R,8\text{-}R'\text{-}7,8\text{-}C_2B_9H_{10})]^-$, wherein M is selected from a radioisotope of technetium and rhenium and R and R' are independently selected from $(CH_2)_nCO_2H$, $NH_2$ and $NH\text{-}NH_2$, n is 0–50. In more specific embodiments of the present invention, the functional derivative has the formula $[M(CO)_3(\eta^5\text{-}7\text{-}R\text{-}7,8\text{-}C_2B_9H_{10})]^-$, wherein R is selected from $(CH_2)_nCO_2H$, $NH_2$ and $NH\text{-}NH_2$, and n is 0–10. In even more specific embodiments, the functional derivative has the formula $[M(CO)_3(\eta^5\text{-}7\text{-}R\text{-}7,8\text{-}C_2B_9H_{10})]^-$, wherein R is $(CH_2)_nCO_2H$ and n is 0–10. In further embodiments, the present invention includes metal-carborane complexes having the formula $[M(CO)_3(\eta^5\text{-}7\text{-}R\text{-}7,9\text{-}C_2B_9H_{10})]^-$, $[M(CO)_3(\eta^5\text{-}9\text{-}R'\text{-}7,9\text{-}C_2B_9H_{10})]^-$ or $[M(CO)_3(\eta^5\text{-}7\text{-}R,9\text{-}R'\text{-}7,9\text{-}C_2B_9H_{10})]^-$, wherein M is selected from a radioisotope of technetium and rhenium and R and R' are independently selected from $(CH_2)_nCO_2H$, $NH_2$ and $NH\text{-}NH_2$, and n is 0–50.

In further embodiments of the present invention, the functional derivatives comprise a carborane selected from the group consisting of compound 13 (FIG. 3) and 14 (Example 14), and the corresponding deprotected compounds.

Some of the compounds of the invention may have at least one asymmetric center. Where the compounds according to the invention have one asymmetric center, they may exist as enantiomers. Where the compounds of the invention possess two or more asymmetric centers, they may additionally exist as diastereomers. It is to be understood that all such isomers and mixtures thereof in any proportion are encompassed within the scope of the present invention.

Uses

The invention also includes the use of the metal-carborane complexes prepared using the method of the invention for the preparation of radiopharmaceuticals. In particular, the functional derivatives of the metal carborane complexes may be conjugated to a biological targeting ligand and the resulting complex used as a radiopharmaceutical or to prepare a pharmaceutical composition by mixing with a pharmaceutically acceptable carrier or diluent.

Accordingly, the present invention provides a method of preparing a radiopharmaceutical comprising conjugating a metal carborane complex prepared using the method of the invention to a biological targeting ligand. The invention also includes a method of preparing a radiopharmaceutical composition comprising conjugating a metal carborane complex prepared using the method of the invention to a biological targeting ligand and combining with a pharmaceutically acceptable carrier or diluent. In an embodiment of the invention, the metal carborane complex is selected from the novel metal carborane complexes of the invention.

In a further embodiment of the present invention, there is included a use of a metal-carborane complex prepared using the method of the invention as a radiopharmaceutical. Therefore the present invention also includes radiopharmaceutical compositions comprising a metal carborane complex prepared using the method of the invention and a pharmaceutically acceptable carrier.

The compositions containing the metal carborane complexes prepared using the method of the invention can be prepared by known methods for the preparation of pharmaceutically acceptable compositions which can be administered to subjects, such that an effective amount of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The term an "effective amount" "of an agent as used herein is that amount sufficient to effect beneficial or desired results, and, as such, an "effective amount" depends upon the context in which it is being applied. For example, in the context of administering an agent for use as a radiopharmaceutical or for radioimaging, an effective amount of an agent is, for example, an amount sufficient to achieve effective image of the tissue or organ of interest.

In accordance with the methods of the invention, the described radiopharmaceutical compositions may be administered to a patient in a variety of forms depending on the radiopharmaceutical application, as will be understood by those skilled in the art.

The dosage of the compositions of the invention can vary depending on many factors such as the pharmacodynamic properties of the active ingredient, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors.

The following non-limiting examples are illustrative of the present invention:

EXAMPLES

Materials and General Procedures for Examples 1–10

All reactions were carried out under an atmosphere of dry argon or nitrogen using standard Schlenk line techniques. With the exception of decaborane, which was purchased from Katchem Ltd. and used as received, reagents were obtained from Aldrich Chemical Co. The reagent, [nido-7,8-$C_2B_9H_{12}$]$^-$ was prepared as previously described.[22] Petroleum ether refers to that fraction of boiling point 40–60° C. THF was purified by distillation on benzophenone-sodium under nitrogen while acetonitrile was distilled from $CaH_2$ under $N_2$. TLC was performed using Merck silica gel F-254 on aluminum plates. Solvent systems are reported as v/v mixtures. Compounds were visualized using a 0.1% mixture of $PdCl_2$ in hydrochloric acid (3 M) followed by heating with a heat gun. Merck 60 $GF_{254}$ (7730) on silica gel plates and Silicycle silica gel (70–230 mesh) were used for preparative thin-layer chromatography and flash chromatography respectively.

The NMR spectra were recorded at ambient temperature on Bruker AV200 and AV300 spectrometers. Chemical shifts (δ) are relative to tetramethylsilane as internal standard for $^1H$ NMR and $BF_3.OEt_2$ as external reference for $^{11}B$ NMR. Cl refers to chemical ionization mass spectrometry, El refers to electron impact mass spectrometry and ES refers to electrospray mass spectrometry, which was performed on a Fisons Platform quadrupole instrument using samples dissolved in 50/50 $CH_3OH$—$H_2O$ mixtures. IR spectra were run on a Bio-Rad FTS-40 FT FTIR spectrometer. HPLC experiments were run on a Varian Prostar Model 230 HPLC using a MicroSorb-MV column (25 cm, 8μ, G6 10002-4) with a mobile phase consisting of 70% $CH_3OH$—30% $H_2O$. The flow rate was maintained at 0.5 mL/min.

Caution: $^{99}Tc$ is a weak β$^-$emitter (E=292 keV, $t_{1/2}$=2.12× $10^5$ yrs).

Example 1
Synthesis of $[NEt_4]_2[M(CO)_3Br_3]$

The title compound was prepared using the method reported in Alberto et al. 1995.[15] The pattern of the vCO IR stretches for $[NEt_4][M(CO)_3Br_3$ (M=Re, $^{99}Tc$) prepared were indicative of the $C_{3v}$ symmetry of the products and the stretching frequencies were similar to the reported values for the corresponding chloro complexes.[15]

Example 1A
Synthesis of $[NEt_4][Re(CO)_3(\eta^5$-7,8-$C_2B_9H_{11})]$, Compound 1

$[(CH_3)_3NH][nido$-7,8-$C_2B_9H_{12}]$ (96.8 mg, 0.5 mmol) was dissolved in THF (20 mL) under argon and cooled to –20°C. with an acetone-dry ice bath. TlOEt (267 mg, 76 μL, 1.05 mmol) was added using an Eppendorff pipet previously filled with argon. With vigorous stirring under argon and protected from light, the reaction mixture was allowed to warm to room temperature over 1 hr. The ensuing precipitate was isolated by a combination of careful decantation and extraction of the remaining solvent using a syringe. The precipitate was rinsed twice with pentane (7 mL), then dried under vacuum. To the yellow solid, $[NEt4]_2[ReBr_3(CO)_3]$ (193 mg, 0.25 mmol) and THF (10 mL) were added under argon and the mixture heated to reflux overnight. After cooling to room temperature, the heterogenous solution was filtered through celite, and the residue rinsed with THF. The filtrate was concentrated under reduced pressure and the product isolated from the resulting yellow oil by either flash chromatography or preparative thin layer chromatography ($CH_2Cl_2$). The product, a colourless solid was further purified by recrystalization from a dichloromethane-ether mixture (124 mg, 93%). Mp: 220° C. (decomp.); TLC $R_f$ 0.41 ($CH_2Cl_2$); IR (KBr): v 3043, 3014, 2996, 2588, 2556, 2528, 2510, 2494, 2009, 1896, 1865; $^1H$ NMR (200 MHz, $CD_2Cl_2$): δ 3.19 (q, J=7.3 Hz, 8H, $CH_2$), 2.97 (br s, 2H, CH), 1.33 (m, 12H, $CH_3$); $^{13}C$ NMR (50.3 MHz, $CD_2Cl_2$): δ 198.8, 53.1, 32.7, 7.8; $^{11}B$ (96.3 MHz, $CD_2Cl_2$): δ –7.99, –11.62, –15.83, –22.92, –24.16; MS (ES, negative): m/z= 403.1[M]$^-$; Anal. Calcd. for $C_{13}H_{31}O_3B_9ReN$ (532.89): C, 29.30; H,5.86. Found: C, 29.43; H, 6.08.

Example 2
Synthesis of $[NEt_4][Tc(CO)_3(\eta^5$-7,8-$C_2B_9H_{11})]$, Compound 5

$[(CH_3)_3NH][nido$-7,8-$C_2B_9H_{12}]$ (48 mg, 0.25 mmol) was dissolved in THF (10 mL) under nitrogen and cooled to –30° C. with an acetone-dry ice bath. TlOEt (134 mg, 38 μL, 0.525 mmol) was added using an Eppendorff pipette previously filled with nitrogen. With vigorous stirring under nitrogen and protected from light, the reaction mixture was allowed to warm to room temperature over an hour. The ensuing precipitate was isolated by a combination of careful decantation and extraction of the remaining solvent using a syringe. The precipitate was rinsed once with THF (5 mL) then dried under vacuum. To the yellow solid $[NEt_4]_2[TcBr_3(CO)_3]$ (85 mg, 0.125 mmol) and THF (5 mL) were added under nitrogen and the mixture refluxed overnight. After cooling to room temperature, the solution was filtered and the residue rinsed with THF. The filtrate was concentrated under reduced pressure and the product, a beige powder (45 mg, 80%), was isolated by preparative thin layer chromatography ($CH_2Cl_2$). TLC $R_f$ 0.25 ($CH_2Cl_2$/MeOH:⁴⁄₁); IR (KBr): v 2959, 2581, 2523, 2503, 2016, 1918, 1908; $^1H$ NMR (200 MHz, $CD_2Cl_2$): δ3.20 (q, J=7.3 Hz, 8H, $CH_2$), 2.72 (br s, 2H, CH), 1.34 (m, 12H, $CH_3$); $^{13}C$ NMR (50.3 MHz, $CD_2Cl_2$): δ53.2, 35.3, 7.80; $^{11}B$ (96.3 MHz, $CD_2Cl_2$): δ –7.52, –8.22, –10.18, –13.26, –20.75, –22.42; MS (ES, negative): m/z=315.0[M]$^{31}$.

Example 3
Synthesis of Benzyl Pent-4-ynoate,[23] Compound 7

4-pentynoic acid (5.0 g, 48.42 mmol) was dissolved in a solution of dry acetonitrile (100 mL) followed by the dropwise addition of 1,8-diazabicyclo [5,4,0]undec-7-ene (DBU) (8.38 mL, 53.79 mmol ). Freshly distilled benzyl bromide (6.68 mL, 56.07 mmol) was added slowly to the stirring mixture, and the reaction maintained at room temperature overnight. The reaction mixture was transferred to a separatory funnel and diluted with diethyl ether (60 mL). The organic layer was washed with 1M HCl (3×40 mL), and all aqueous layers combined, and further washed with ether (3×60 mL). The organic fractions were combined, dried over magnesium sulfate, filtered, and the solvent removed in vacuo giving a light yellow oil. Vacuum distillation (2 mm Hg/ b.p. 111° C.) yielded the desired product (8.57 g, 94%). TLC $R_f$ 0.67 (1:1 ether:hexanes); IR (neat): v 3297, 3090, 3068, 2956, 2928, 2897, 2122, 1739, 1164; $^1H$ NMR (200 MHz, $CDCl_3$): δ 7.45–7.26 (m, 5H, H-aryl), 5.14 (s, 2H, $CH_2Ph$), 2.56 (m, 4H, $CH_2CH_2$), 1.96 (br s, 1H, CH); $^{13}C$ NMR (50 MHz, $CDCl_3$): δ 171.49, 135.65, 128.47, 128.14, 82.32, 69.04, 66.41, 33.25, 14.23; MS (El): m/z=189[M+H]$^+$.

Example 4
Synthesis of Benzyl 3-(1',2'-dicarboclosododecaboran-1'-yl) propanoate, Compound 8

Decaborane (3.25 g, 26.6 mmol) was dissolved in dry acetonitrile (50 mL) and stirred under nitrogen for 13 hours prior to the dropwise addition of 4 (5.0 g, 26.6 mmol). The reaction mixture was brought to reflux for four days after which the solution was allowed to cool to room temperature and the solvent removed in vacuo giving a yellow oil. The oil was taken up in diethylether (100 mL) and washed three times with 1M NaOH (50 mL). The organic layer was collected, dried over magnesium sulfate, filtered and the solvent removed in vacuo. The resulting oil was taken up in a minimal amount of hexanes and subjected to silica gel chromatography with hexanes-ethyl acetate (9:1) as the eluent. The product (4.89 g, 60%) was isolated as a white amorphous solid. m.p. =80–81° C.; TLC $R_f$ 0.58 (1:1 ether:hexanes); IR (KBr): v 3064, 3034, 2945, 2929, 2879, 2583, 1729; $^1$H NMR (300 MHz, CDCl$_3$): δ 7.41–7.34 (m, 5H, H-aryl), 5.14 (s, 2H, PhCH$_2$), 3.69 (br s, 1H, CH), 2.59 (m, 4H, CH$_2$CH$_2$); $^{13}$C NMR (75.5 MHz, CDCl$_3$): δ 171.3, 135.3, 128.8, 128.7, 128.6, 74.1, 67.2, 61.6, 33.6, 32.8; $^{11}$B NMR (160 MHz, CDCl$_3$): δ −2.50, −5.97, −9.85, −12.01, −12.68, −13.37; MS (Cl): m/z=324[M+NH$_3$].

Example 5
Synthesis of 3-(1',2'-dicarbaclosododecaboran-1'-yl) propanoic acid, Compound 9

The reaction vessel was charged with 10% palladium on carbon (320 mg) and compound 8 (3.21 g, 10.47 mmol) in absolute ethanol (50 mL) and glacial acetic acid (2 drops). In a Parr Hydrogenator, the mixture was subjected to an atmosphere of hydrogen (2 atm.) with shaking for 2 hours. The mixture was filtered through Celite, and the residue washed with absolute ethanol (3×20 mL). The filtrates were combined, the solvent evaporated in vacuo and the resulting solid dried under high vacuum (2.30 g, 99%). m.p.= 145–146° C; TLC $R_f$ 0.39 (1:1 ether:hexanes); IR (KBr): v 3448, 3054, 2999, 2929, 2859, 2586, 1702; $^1$H NMR (300 MHz, CDCl$_3$): δ 3.67 (br s, 1H, CH), 2.65–2.54 (m, 4H, CH$_2$CH$_2$); $^{13}$C NMR (75.5 MHz, CDCl$_3$): δ 177.1, 73.7, 61.7, 33.3, 32.5; $^{11}$B NMR (160 MHz, CDCl$_3$): δ −2.51, −5.96, −9.80, −11.93, −12.57, −13.31 MS (ES, negative): m/z=215.1[M−H+]$^−$.

Example 6
Synthesis of [PMePh$_3$]rac-[nido-7-(CH$_2$CH$_2$CO$_2$H)-7,8-C$_2$B$_9$H$_{11}$], Compound 10

Compound 9 (216 mg, 1.0 mmol) was added to a solution of potassium hydroxide (297 mg, 4.5 mmol) in absolute ethanol (6.7 mL) and the reaction mixture heated to reflux for 24 hrs. After cooling to room temperature, carbon dioxide was bubbled through the solution to precipitate the excess of KOH as potassium carbonate. The white suspension was filtrated through celite and the residue rinsed with absolute ethanol. After evaporation of the filtrate under reduced pressure, the resulting oil was acidified to pH 2 with HCl (1.0 M). The water was removed under vacuum and the resulting white solid re-dissolved in distilled water (4 mL) and a 2.0 M aqueous solution of MePPh$_3$Br (547 mg, 1.5 mmol) was added dropwise. The solution was cooled to 0° C. and the resulting precipitate isolated by filtration. The residue, after lyophilization overnight, was dissolved in CH$_2$Cl$_2$, filtered through a plug of glass wool, and, after removal of the solvent, the resulting solid was recrystallized from a mixture of CH$_2$Cl$_2$ and petroleum ether yielding the product as a colourless solid (486 mg, >99%). m.p. 160° C. decomp; TLC $R_f$ 0.82 (4:1 CH$_2$Cl$_2$:CH$_3$OH); IR (KBr): δ 3440, 3059, 2984, 2915, 2855, 2512, 1711, 1438, 1115, 900; $^1$H NMR (200 MHz, CD$_2$Cl$_2$): δ 7.88–7.57 (m, 15H, H-aryl), 2.84 (d, J=13 Hz, 3H, P—CH$_3$), 2.43–2.33 (m, 2H, CH$_2$), 1.90–1.73 (m, 2H, CH$_2$), 1.66 (br s, 1H, CH); $^{13}$C NMR (50.3 MHz, CD$_2$Cl$_2$): δ 179.0, 136.1, 133.7, 133.5, 131.3, 131.0, 35.9, 34.5, 11.2, 10.0; $^{11}$B (CD$_2$Cl$_2$): δ −11.57, −14.40, −17.48, −19.09, −22.43, −34.05, −38,00; MS (ES, negative): m/z=205.2 [M]$^−$; Anal. Calcd. for C$_{24}$H$_{34}$O$_2$PB$_9$, (482.80): C, 59.71; H, 7.10. Found: C, 56.55; H, 6.94.

Example 7
Synthesis of [PMePh$_3$]rac-[Re(CO)$_3$($\eta^5$-7-(CH$_2$CH$_2$CO$_2$H)-7,8-C$_2$B$_9$H$_{10}$)], Compound 11

Compound 10 (97 mg, 0.2 mmol) was dissolved in THF (8 mL) under argon and cooled to −20° C. TlOEt (107 mg, 30.4 μL, 0.42 mmol) was added dropwise using an Eppendorff syringe previously filled with argon. With vigorous stirring under argon and protected from light, the reaction mixture was warmed to room temperature over 2 hours. Pentane (10 mL) was added to the heterogenous mixture and the solution cooled with an acetone-dry ice bath. The ensuing precipitate was isolated by a combination of careful decantation and extraction of the remaining solvent using a syringe. The precipitate was rinsed twice with pentane (10 mL) and then dried under vacuum. To the yellow solid, [NEt$_4$]$_2$[ReBr$_3$(CO)$_3$] (77 mg, 0.1 mmol) and THF (6.5 mL) were added and the reaction mixture heated to reflux overnight under argon. After cooling to room temperature, the solution was acidified to pH 2 with HCl (1 M), filtered through celite, and the residue washed with a 1:1 mixture of THF/1M HCl (5 mL). The filtrate was concentrated under reduced pressure and the resulting brown oil triturated with dichloromethane (5 mL), and the ensuing precipitate removed by filtration. The filtrate was concentrated under reduced pressure and the product, a yellowish powder (74 mg, 99%), was isolated by thin layer chromatography using an eluent composed of CH$_2$Cl$_2$—CH$_3$OH (97:3). The TLC silica was extracted with CH$_2$Cl$_2$, THF and MeOH. m.p. 140° C. (decomp.); TLC $R_f$ 0.70 (9:1 CH$_2$Cl$_2$/MeOH); IR (KBr): v: 3629, 3433, 3060, 2962, 2919, 2871, 2524, 2002, 1893, 1707, 1589, 1439; $^1$H NMR (200 MHz, CD$_2$Cl$_2$): δ 8.07–7.26 (m, 15H, H-aryl), 3.24 (br s, 1H, CH), 2.75 (d, J=13.2 Hz, P—CH$_3$), 2.50–2.45 (m, 2H, CH$_2$), 2.24–2.11 (m, 2H, CH$_2$); $^{13}$C NMR (50.3 MHz, CD$_2$Cl$_2$): δ 199.0, 180.0, 135.9, 133.5, 133.3, 132.7, 131.1, 130.9, 129.5, 129.2, 125.8, 119.7, 117.9, 34.66, 31.17, 30.64; $^{11}$B (96.3 MHz, CD$_2$Cl$_2$): δ −7.37, −10.82, −12.11, −18.03, −19.70, −22.93, −34.60, −38.41; MS (ES, negative): m/z=475.1 [M]$^−$; Anal. Calcd. for C$_{27}$H$_{33}$O$_5$PB$_9$Re, (752.03): C, 43.12; H, 4.42. Found: C, 42.68; H, 4.87.

Example 8
Synthesis of [PMePh$_3$]rac-[Tc(CO)$_3$($\eta^5$-7-(CH$_2$CH$_2$CO$_2$H)-7,8-C$_2$B$_9$H$_{10}$)], Compound 12

Compound 10 (57 mg, 0.117 mmol) was dissolved in THF (5 mL) under nitrogen and cooled to −20 C. TlOEt (94 mg, 27 μL, 0.369 mmol) was added using an Eppendorff syringe previously filled up with nitrogen. With vigorous stirring under nitrogen and protected from light the reaction mixture was allowed to warm to room temperature over two hours. The ensuing precipitate was isolated by a combination of careful decantation and extraction of the remaining solvent using a syringe. The precipitate was rinsed twice with THF and dried under vacuum. To the yellow solid [NEt$_4$]$_2$[TcBr$_3$(CO)$_3$] (40 mg, 0.059 mmol) and THF (7 mL) were added under nitrogen and the mixture heated to reflux overnight. After cooling to room temperature, the solution was acidified to pH 2 with HCl (1M), filtered through celite, and the residue rinsed with a 1:1 mixture of THF/1M HCl. The filtrate was concentrated under reduced pressure and the product, a beige powder, was isolated by thin layer chromatography using an eluent composed of CH$_2$Cl$_2$—CH$_3$OH (97:3). The TLC silica was extracted with CH$_2$Cl$_2$, THF and CH$_3$OH (93%). TLC $R_f$ 0.64 (9:1 CH$_2$Cl$_2$/CH$_3$OH); IR (KBr) v 3627; 3295, 3059, 2956, 2917, 2870, 2529, 2009, 1911, 1727; $^1$H NMR (200 MHz, CD$_2$Cl$_2$): δ 7.76–7.44 (m, 15H, H-aryl), 2.25 (m, 4H, CH$_2$CH$_2$), 2.00 (d, J=13.2 Hz, 3H, P—CH$_3$); $^{11}$B (96.3 MHz, CD$_2$Cl$_2$): δ −6.81, −8.92, −10.81, −12.25, −14.13, −18.62, −21.77; MS (ES, negative): m/z=388.1[M]$^−$.

Example 9
Synthesis of [Na]rac-[Re(CO)$_3$($\eta^5$-7-(CH$_2$CH$_2$CO$_2$H)-7,8-C$_2$B$_9$H$_{10}$)]$^{24}$ A sample of [PMePh$_3$]rac-[Re(CO)$_3$($\eta^5$-7-(CH$_2$CH$_2$CO$_2$H)-7,8-C$_2$B$_9$H$_{10}$)] was dissolved in a mixture of CH$_3$CN—H$_2$O (60:40) and subjected to ion exchange on a strong cation-exchange resin column (MALLINCKRODT Amberlite CG-120 100–200 mesh). The volatiles were removed by evaporation under reduced pressure, and the residue dried on a lyophilizer to yield the respective sodium salt. HPLC t$_R$=6.21 (95.2%); MS (ES, negative): m/z=475.1 [M]$^-$.

Example 10
Synthesis of [K]rac-[Re(CO)$_3$[$\eta^5$-7-(CH$_2$CH$_2$CO$_2$H)-7,8-C$_2$B$_9$H$_{10}$], in water The sodium salt of compound 10 (171 mg, 0.7 mmol) and potassium hydroxide (370 mg, 5.6 mmol) were dissolved in deionized water (3 mL). [NEt$_4$]$_2$[ReBr$_3$(CO)$_3$] (1.1 mg, 1.4 mmol) was added and the reaction mixture was heated under reflux overnight. After cooling to room temperature, the solution was acidified to pH 1 using HCl (1 M), and the heterogenous solution filtered through celite. The filtrate was evaporated, re-dissolved in water and the pH adjusted to between 5 and 6 with HCl (6 M). The resulting precipitate was filtered through Celite and the solution evaporated under reduced pressure. The remaining residue was further lyophilized leaving a white powder. HPLC t$_R$=6.72 {[K]rac-[Re(CO)$_3$[$\eta^5$-7-(CH$_2$CH$_2$CO$_2$H)-7,8-C$_2$B$_9$H$_{10}$]}, t$_R$=7.01 {[K]rac-[nido-7-(CH$_2$CH$_2$CO$_2$H)-7,8-C$_2$B$_9$H$_{11}$]}; MS (ES, negative): m/z=475.1[M]$^-$.

Materials and General Procedures for Examples 11–16

All commercial reagents were used as supplied. THF and Et$_2$O were distilled under nitrogen from sodium and benzophenone while CH$_2$Cl$_2$ was distilled from CaH$_2$. Orthocarboranes were purchased from Katchem Ltd. (Czech. Rep.), while meta-carborane was purchased from Dexsil Corp. (Hamden, Conn.). CO$_2$(g), which was generated by sublimation of CO$_2$(s), was passed through a column of Drierite® prior to its addition to a reaction. Analytical TLC was performed on silica gel 60-F$_{254}$ (Merck). Boron compounds were visualized with 0.1% PdCl$_2$ in hydrochloric acid (3.0 M), which upon heating gave dark brown spots. Hydrazine derivatives were visualized using a ninhydrin solution, which consisted of 0.3% of ninhydrin in n-butanol containing 3% acetic acid.

NMR spectroscopy experiments were performed on Bruker Avance AV300 and DRX500 spectrometers. TMS and BF$_3$-Et$_2$O were used as internal standards for $^1$H and $^{11}$B spectra respectively. For NMR assignments, b refers to broad signals, s refers to singlets and m refers to multiplets. Electrospray mass spectrometry experiments were performed on a Fisons Platform quadrupole instrument. Samples were dissolved in 50:50 CH$_3$CN/H$_2$O and, for compounds run in negative ion detection mode, one drop of 0.10 M NH$_4$OH was added. Microanalyses were performed by Guelph Chemical Laboratories (Guelph, Ontario, Canada). IR spectra were run on a Bio-Rad FTS-40 FTIR spectrometer.

Example 11
Synthesis of 1-[(N,N'((tert-butyloxy)carbonyl)hydrazino)]-7,8-dicarba-closo-dodecaborane, 15.

MeLi (4.70 mL, 6.53 mmol, 1.39 M in diethyl ether) was added dropwise over 5 minutes to a solution of 7,8-dicarba-closo-dodecaborane (2, 1.00 g, 6.93 mmol) in ether (125 mL) at 0° C. The reaction was maintained at 0° C. for an additional 45 minutes at which time, the solution was added dropwise over 15 minutes to a solution of DBAD (4.00 9, 17.37 mmol) in ether (100 mL) under argon atmosphere. After the complete addition of the carborane, the reaction heated to reflux for 2.5 hours at which point the reaction was quenched with the addition of water (100 mL). The solvent was removed by rotary evaporation, and the resulting solution acidified through dropwise addition of HCl (1.0 M) affording a white precipitate. The solution was extracted with ethyl acetate (3×100 mL) and the organic layers combined, dried over MgSO$_4$, and the solvent removed by rotary evaporation. Residual water was removed by the addition and subsequent evaporation of 9:1 CHCl$_3$/toluene mixtures (5×50 mL). Excess DBAD was removed by triturating the yellow solid with cold pentane (5×50 mL), leaving a colourless solid, which was further purified by silica gel chromatography (gradient elution; 100% hexanes to 1:3 diethyl ether/hexanes). The main product isolated from the column was recrystallized from petroleum ether affording a white solid (2.01 g, 84%). TLC R$_f$ (1:5 diethyl ether/pet. ether)=0.38; mp 171 –174° C. (decomp.); $^1$H NMR (acetone-d$_6$, 300 MHz): δ 1.391, 1.422 (s, CH$_3$), 0.91–3.1 (b, BH), 5.084, 5.233 (bs, CH), 8.241, 8.808 (bs, NH); $^{13}$C NMR (acetone-d$_6$, 125.77 MHz): δ 27.08, 27.46 (CH$_3$), 63.86 (CH), 81.12, 83.80 (C(CH$_3$)$_3$), 87.44 (CN), 151.69 (NCO), 155.01 (NHCO); $^{11}$B{$^1$H} NMR (CDCl$_3$, 96.3 MHz): δ −3.51, −5.00, −7.43, −11.03, −12.66, −15.05; IR (KBr, cm$^{-1}$): 3321, 3077, 2612, 1754, 1719; MS/ESI: 373.3 [M−H]$^-$ with the expected isotopic distribution; Anal. Calcd for C$_{12}$B$_{10}$H$_{30}$N$_2$O$_4$: C, 38.49; H, 8.07; N, 7.48. Found: C, 38.10; H, 8.12; N, 7.40.

Example 12
Synthesis of 7-[(N,N'((tert-butyloxy)carbonyl)hydrazino)]-7,8-dicarba-closo-dodecaborane-8-carboxylic acid, 13 n-BuLi (1.75 mL, 2.80 mmol, 1.6 M in hexanes) was added dropwise over a period of 5 minutes to a solution of compound 15 (0.50 g, 1.34 mmol) in 5:1 THF/ether (60 mL) at 0° C. After 45 minutes the temperature was lowered to −78° C. and CO$_2$ bubbled into the solution for 3.5 hours. The temperature was allowed to warm to room temperature and the solvent removed in vacuo. Water (50 mL) was added and the solution acidified by dropwise addition of HCl (1.0 M) until a precipitate appeared (pH=3). The solution was extracted with ethyl acetate (3×50 mL), and the organic layers combined, dried over MgSO$_4$, and evaporated leaving a colourless oil. Suspension of the oil in a 4:1 mixture of pentane/ether afforded a white precipitate, which was washed with the pentanelether mixture (4×50 mL) leaving the product as a white solid (371 mg, 65%); TLC R$_f$ (1:9 CH$_3$OH/CH$_2$Cl$_2$)=0.14; mp 131° C. (decomp.); $^1$H NMR (acetone-d$_6$, 300 MHz): δ1.438, 1.472 (s, CH$_3$), 1.220–2.810 (b, BH), 8.335, 8.904 (s, NH); $^{13}$C NMR (acetone-d$_6$+2 drops of DMSO-d$_6$, 50.3 MHz): δ 27.50, 27.80, 27.95 (CH$_3$), 63.57, 64.76 (CCO$_2$H), 80.90, 81.16, 83.79 (C(CH$_3$)$_3$), 87.83 (CN), 151.74 (BocC(O)), 154.00 (CO$_2$H), 155.04 (BocC(O)); $^{11}$B{$^1$H} NMR (acetone-d$_6$, 96.3 MHz): δ −3.58, −6.20, −11.05, −13.49; IR (KBr): 3380, 2578, 1713, 1650. MS/ESI: 835.5 [2M−H]$^-$, 417.3[M−H]$^-$, 408.4 [M−B]$^-$, 373 [M-CO$_2$H]$^-$ with the expected isotopic distribution; Anal. Calcd for C$_{13}$H$_{30}$B$_{10}$N$_2$O$_6$: C, 37.31; H, 7.23. Found: C, 34.33; H, 7.59.

Example 13
Synthesis of 1-[(N,N'((tert-butyloxy)carbonyl)hydrazino)]-7,9-dicarba-closo-dodecaborane.

n-BuLi (5.00 mL, 6.93 mmol; 1.39 M in hexanes) was added to 7,9-dicarba-closo-dodecaborane (meta-carborane, 1.00 g, 6.93 mmol) in dry diethyl ether (125 mL) at 0° C.

under argon. After 45 minutes, the solution containing the anion was added slowly to DBAD (3.19 g, 13.86 mmol) in dry diethyl ether (100 mL). The reaction was subsequently heated under reflux for 2.5 hours whereupon it was cooled to room temperature and quenched by the addition of water (10 mL). Diethyl ether was removed under reduced pressure and the mixture extracted with ethyl acetate (100 mL), which in turn was washed with water (1×100 mL), 0.1 M HCl (2×100 mL), and brine (2 x 100 mL). The organic layers were combined, dried over $MgSO_4$ and the solvent concentrated under reduced pressure. The product, an amorphous white solid (1.94 g, 75%), was further purified by silica gel chromatography (gradient elution; from petroleum ether to 1:9 ethyl acetate/petroleum ether): TLC $R_f$ (1:9 ethyl acetate/pet. ether)=0.36; mp 143–144° C.; $^1H$ NMR (acetone-$d_6$, 300 MHz): δ 1.242, 1.280 (s, $CH_3$), 1.198–2.87 (b, BH), 3.541, 4.445 (bs, CH), 8.056, 8.503 (bs, NH); $^{13}C$ NMR (acetone-$d_6$, 125.77 MHz): δ27.22, 27.57 ($CH_3$), 53.12 (CH), 80.22, 80.78, 82.30, 82.51 ($C(CH_3)_3$), 89.37 (CN), 151.70, 151.87 (BocC(O)), 154.25, 154.50 (BocC (O)); $^{11}B\{^1H\}$ NMR (acetone-$d_6$, 96.3 MHz): δ −4.79, −11.27, −12.97, −15.68; IR (KBr): 3317, 3061, 2972, 2607, 1739, 1722.1; MS/ESI: 373.3$[M-H]^{-1}$; Anal. Calcd for $C_{12}B$,$OH_{30}N_2O_4$: C, 38.49; H, 8.07; N, 7.48. Found: C, 38.91; H, 8.42; N, 7.47.

Example 14
Synthesis of 1-[(N,N'((tert-butyloxy)carbonyl)hydrazino)]-7,9-dicarba-closo-dodecaborane-7-carboxylic acid, 14.

n-BuLi (1.75 mL, 2.80 mmol) was added dropwise over a period of 5 minutes to the product from Example 13 (0.50 g, 1.34 mmol) in dry THF (100 mL) under argon at 0° C. for 45 minutes. The temperature of the reaction was subsequently lowered to −78°C. and dry $CO_2(g)$ was bubbled into the solution with rigorous stirring. After 3.5 hours, the reaction was allowed to warm to room temperature and acidified with 1M HCl (pH=3). The solvent was removed under reduced pressure and the yellowish residue re-dissolved in ethyl acetate (50 mL) and extracted with brine (3×50 mL). The organic phase was dried over $MgSO_4$ and evaporated to dryness. The resulting yellow oil was further purified by flash chromatography through silica gel (gradient elution; from $CH_2Cl_2$ to 5:95 $CH_3OH/CH_2Cl_2$) yielding an amorphous solid (0.41 g, 73%): TLC $R_f$ (1:4 $CH_3OH/ CH_2Cl_2$)=0.57; mp 156–159° C.; $^1H$ NMR (acetone-$d_6$, 300 MHz): δ 1.353, 1.391, 1.430 (s, $CH_3$), 0.95–4.25 (b, BH), 8.064, 8.507 (bs, NH); 13C NMR (acetone-$d_6$, 125.77 MHz): δ 27.21, 27.55 ($CH_3$), 70.12 ($CCO_2H$), 80.45, 81.09, 82.66, 82.84 ($C(CH_3)_3$), 89.12 (CN), 151.81, 154.52 (BocC(O)), 161.80 ($CO_2H$); $^{11}B\{^1H\}$ NMR (acetone-$d_6$, 96.3 MHz): δ −4.36, −8.90, −10.52, −12.76; IR (KBr): 3317, 3185, 2986, 2939, 2617, 1753, 1721; MS/ESI: 373.3$[M-H]^-$, 835.5$[2M-H]^-$; Anal. Calcd for $C_{13}B_{10}H_{30}N_2O_6$: C, 37.31; H, 7.23; N, 6.69. Found: C, 36.96; H, 7.61; N, 6.20.

Example 15
General Method for the Preparation of the Nido-Derivatives

The nido salts of compounds 13 and 14 may be prepared by refluxing the corresponding closo compounds in KOH and EtOH for 24 hours. The remaining KOH is quenched with water and the products may be isolated as colourless solids by precipitation as their $[MePPh_3]^+$ salts.

Example 16
Synthesis of Na[$^{99m}Tc(CO)_3(\eta^5\text{-}7,8\text{-}C_2B_9H_{11})$] and Na{rac-[$^{99m}Tc(CO)_3(\eta^5\text{-}7\text{-}CH_2CH_2CO_2H\text{-}7,8\text{-}C_2B_9H_{10})$]} from $Na^{99m}TcO_4$ In a 10 mL sealed serum vial were introduced $NaBH_4$ (5 mg, 130 μmol, ≈22.10$^6$ eq) and $Na_2CO_3$ (4 mg, 38 μmol, ≈6.10$^6$ eq). The vial was flushed with CO for 10–20 min. $Na^{99m}TcO_4$ (3 mCi) dissolved in saline (3 mL of 0.9% w/w NaCl in water) was added. The reaction was heated 40 min at 85° C. (temperature of the water bath). For safety reason, a 20 mL guard syringe was kept through the septum to buffer the $H_2$ release. The colorless solution was cooled down to room temperature using an ice bath. A sample was taken up to observe the formation of $[Tc(CO)_3(OH_2)]^+$ by TLC scanning (95:5 $CH_3OH/$ 12M HCl, Rf≈0.4). The solution was splinted into two aliquots (1.5 mCi, 1.5 mL) and added to two 10 mL serum vials containing $(Me_3NH)(C_2B_9H_{12})$ (193.53 g/mol, 10$^5$ eq, 0.289 μmol, 56 μg) or $K(C_2B_9H_{11}$—$CH_2$—$CH_2$—$CO_2H)$ (244.57 g/mol, 10$^5$ eq, 0.289 μmol, 71 μg). heated at 85° C. for 2 h and cooled down to room temperature with an ice bath. The solutions were acidified with 1 M HCl and analyzed by TLC scanning and HPLC according to the conditions below. The TLC and HPLC retention times and profiles of the radioactive compounds were identical to authentic standards prepared and characterized separately.

| $(Me_3NH)(C_2B_9H_{12})$ | $K(C_2B_9H_{11}$—$CH_2$—$CH_2$—$CO_2H)$ |
|---|---|
| Acidification to pH ≈ 7 | Acidification to pH ≈ 2 |
| TLC scanning (9:1 $CH_2Cl_2/CH_3OH$) $R_f$ ≈ 0.40 | TLC scanning (9:1 $CH_2Cl_2/CH_3OH$) $R_f$ ≈ 0.40 |
| HLPC (40:60 $CH_3OH/H_2O$) | HLPC (70:30 $CH_3OH/H_2O$) |

Note:
1. HPLCs ran on an analytical Varian HPLC connected to a beta-radiation detector and equipped with a $C_{18}$ semi-Preparative MicroSorb 250 × 10 300–5 column. All runs were isocratic at 1.5 mL/min.
2. Control injection of $Na^{99m}TcO_4$ in HPLC (40:60 $CH_3OH/H_2O$) and (70:30 $CH_3OH/H_2O$)
3. Control injection of $Na[Re(CO)_3(C_2B_9H_{11})]$ in HPLC (40:60 $CH_3OH/H_2O$)
4. Control injection of $(Me_3NH)(C_2B_9H_{12})$ in HPLC (40:60 $CH_3OH/H_2O$)
5. Control injection of $Na[Re(CO)_3(C_2B_9H_{11}$—$CH_2$—$CH_2$—COOH)] in HPLC (70:30 $CH_3OH/H_2O$)
6. Control injection of $K(C_2B_9H_{11}$—$CH_2$—$CH_2$—$CO_2H)$ in HPLC (70:30 $CH_3OH/H_2O$)

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Full Citations for References Referred to in the Specification
1. Alberto, R.; Schibli, R.; Egli, A.; Schubiger, P. A.; Abram, U.; Kaden, T. A. J. *Am. Chem. Soc.* 1998, 120, 7987.
2. Alberto, R.; Schibli, R.; Schubiger, P. A.; Abram, U., Kaden, T. Polyhedron, 1996, 15,1079; Alberto, R.; Schibli, R.; Egli, A.; Schubiger, P. A.; Herrmann, W. A.; Artus, G.; Abram, U.; Kaden, T. A. *J. Organomet. Chem.* 1995, 493,119.
3. Jurisson, S. S.; Lydon, J. D. *Chem. Rev.* 1999, 99, 2205.
4. Alberto, R.; Schibli, R.; Schubiger, A. P.; Abram, U.; Pietzsch, H. -J.; Johannsen, B. J. *Am. Chem. Soc.* 1999, 121, 6076. Abram, U.; Abram, S.; Schibli, R.; Alberto, R.; Dilworth, J. R. *Polyhedron* 1998, 17(8), 1303.
5. Schibli, R.; Alberto, R.; Abram, U.; Abram, S.; Egli, A.; Schubiger, P. A.; Kaden, T. A. *Inorg. Chem.* 1998, 37, 3509.
6. Minutolo, P.; Katzenellenbogen, J. A. *J. Am. Chem. Soc.* 1998, 120, 4514. Minutolo, P.; Katzenellenbogen, J. A. *J. Am. Chem. Soc.* 1998, 120,13264; Minutolo, P.; Katzenellenbogen, J. A. *Angew. Chem. Int. Ed. Engl.* 1999, 38(11), 1617.
7. Top, S.; Kaloun, E. B.; Jaouen, G. *J.Am. Chem. Soc.* 2000, 122, 736.
8. Cesati III, R. R.; Katzenellenellenbogen, J. A. *J. Am. Chem. Soc.* 2001, 123, 4093.
9. Hawthorne, M. F.; Young, D. C. and Wegner, P. A. *J. Am. Chem. Soc.,* 1965, 87,1818.
10. Hawthorne, M. F.; Andrews, T. D. *J. Am. Chem. Soc.* 1965, 87, 2496.
11. Ellis, D. D.; Jelliss, P. A.; Stone, F. G. A. *Organometalics* 1999, 18, 4982.
12. Hawthorne, M. F.; Maderna, A. *Chem. Rev.* 1999, 99, 3421–3434.
13. Hawthorne, M. F.; Varadarajan, A.; Knobler, C. B.; Chakrabarti, S. *J. Am Chem. Soc.* 1990,112, 5365.
14. Dilworth, J. R.; Parrott, S. *J. Chem. Soc. Rev.* 1998, 27, 43–55.
15. Alberto, R.; Schibli, R.; Egli, A.; Schubiger, P. A.; Herrmann, W. A.; Artus, G.; Abram, U.; Kaden, T. A. *J. Organomet. Chem.* 1995, 493, 119–127.
16. Barth, R. F.; Adams, D. M.;Soloway, A. H.; Mechetner, E. B.;Alam, F.; Anisuzzaman, A.K.M. *Anal. Chem.* 1991, 63, 890.
17. Imahori, Y.; Ueda, S.; Ohmori, Y.; Sakae, K.; Kusuki, T.; Kobayashi, T.; Takagaki, M.; Ono, K.; Ido, T.;Fujii, T. *Jpn Clin. Cancer Res.* 1998, 4(8), 1833.
18. Grimes, R. N. *Carboranes,* Academic Press, N.Y. 1970; Bregadze, V. I. *Chem. Rev.* 1992, 92, 209.
19. Hawthorne, M. F.; Andrews, T. D.; *J. Am. Chem. Soc.* 1968, 90, 879.
20. Blandford, I.; Jeffery, J. C.; Jelliss, P. A.; Stone, F. G. A. *Organometallics* 1998, 17,1402–1411.
21. Stalteri, M. A. *Bioconj. Chem.* 1999, 10, 130.
22. D. A. T. Young, R. J. Wiersma and M. F. J. Hawthorne, *J. Am. Chem. Soc.,* 1974, 93, 5687.
23. Roush, W. R.; Koyama, K.; Curtin, M. L.; Moriarty, K. J. *J. Am. Chem. Soc.* 1996, 118,7502.
24. T. Peymann, C. B. Knobler, S. I. Khan, and M. F. Hawthorne, *Inorg. Chem.,* 2001, 40, 1291.

We claim:

1. A method for preparing metal-carborane complexes comprising reacting salt of the formula:

wherein M is selected from a radioisotope of rhenium, technetium and any other radioisotope that binds in the same fashion, X is any suitable ligand and m is the formal charge for ligand X, with a nido-dicarbollide dianion selected from a compound of the formula [nido-$(C_2B_9H_{11})$]$^{2-}$ and functional derivatives thereof, wherein the functional derative is one that is useful as a radiopharmaceutical.

2. The method according to claim 1, wherein M is selected from a radioisotope of technetium and rhenium.

3. The method according to claim 1, wherein one or more of the CO ligands in the salts of the formula M(CO)$_3$-$(X^m)_3$]$^{(1+3m)}$ salt is substituted with a ligand that is isoelectronic or isolobal therewith.

4. The method according to claim 3, wherein the M(CO)$_3$$(X^m)_3$]$^{(1+3m)}$ salt and nido-dicarbollide dianion are reacted in an aqueous solvent.

5. The method according to claim 1, wherein X is selected from Cl, Br and H$^2$O.

6. The method according to claims 1, wherein the nido-dicarbolide dianion is selected from [nido-7,8-$(C_2B_9H_{11})$]$^{2-}$ and [nido-7,9-$(C_2B_9H_{11})$]$^{2-}$, and functional deratives thereof.

7. The method according to claim 6, wherein the nido-dicarbolide dianion is [nido-7,8-$(C_2B_9H_{11})$]$^{2-}$.

8. The method according to claim 1, wherein the functional derivative of the nido-dicarbollide dianion is a nido-dicarbollide dianion with one or more linker groups attached thereto.

9. The method according to claim 8, wherein the one or more linker groups are attached to carbon atoms in the dicarbollide dianion.

10. The method according to claim 9, wherein the nido-dicarbollide dianion is selected from the formula [nido-7-R-7,8-$(C_2B_9H_{11})$]$^{2-}$, nido-8-R'-7,8-$(C_2B_9H_{11})$]$^{2-}$ and nido-7-R,8-R'-7,8-$(C^2B_9H_{11})$]$^{2-}$, wherein R and R' are, independently, one or more linker groups.

11. The method according to claim 10, wherein R and R' are independently selected from the group consisting of $(CH_2)_nCO_2H$, $NH_2$ and $NH—NH_2$, wherein n is 0–10.

12. The method according to claim 8, wherein the functional derivative of the nido-dicarbollide dianion is a nido-dicarbollide dianion further comprises a biological targeting molecule attached to the one or more linker groups.

13. The method according to claims 1, wherein the functional derivative of the nido-dicarbollide dianion is a nido-dicarbollide dianion incorporated within the structure of a biological targeting ligand.

14. A metal-carborane complex comprising the formula [M(CO)$_3$($\eta^5$-7,8-$C_2B_9H_{10}$)]$^-$, wherein M is a radioisotope of technetium, and functional derivatives thereof, wherein the functional derative is one that is useful as a radiopharmaceutical.

15. A metal-carborane complex comprising the formula [M(CO)$_3$($\eta^5$-7,9-$C_2B_9H_{10}$)]$^-$, wherein M is selected from a radioisotope of technetium and rhenium, and functional derivatives thereof, wherein the functional derative is one that is useful as a radiopharmaceutical.

16. A metal-carborane complex having the formula [M(CO)$_3$($\eta^5$-7-R-7,8-$C_2B_9H_{10}$)]$^-$, [M(CO)$_3$($\eta^5$-8-R'-7,8-$C_2B_9H_{10}$)]$^-$ or [M(CO)$_3$($\eta^5$-7-R,8-R'-7,8-$C_2B_9H_{10}$)]$^-$, wherein M is selected from a radioisotope of technetium and rhenium and R and R' are independently selected from the group consisting of $(CH_2)_nCO_2H$, $NH_2$ and $NH—NH_2$, wherein n is 0–50.

17. A metal-carborane complex having the formula [M(CO)$_3$($\eta^5$-7-R-7,9-$C_2B_9H_{10}$)]$^-$, [M(CO)$_3$($\eta^5$-9-R'-7,9-$C_2B_9H_{10}$)]$^-$ or [M(CO)$_3$($\eta^5$-7-R,9-R'-7,9-$C_2B_9H_{10}$)]$^-$, wherein M is selected from a radioisotope of technetium and rhenium and R and R' are independently selected from $(CH_2)_nCO_2H$, $NH_2$ and $NH—NH_2$, wherein n is 0–50.

18. A method of preparing a radiopharmaceutical comprising conjugating a metal carborane complex prepared using the method according to claims 1 to a biological targeting ligand.

19. A method of preparing a radiopharmaceutical composition comprising conjugating a metal carborane complex prepared using the method according to claims 1 to a biological targeting ligand and mixing with a pharmaceutically acceptable carrier or diluent.

20. The method according to claim 1, wherein M is selected from a radioisotope of technetium, rhenium. rhodium, chromium, molybdenum, manganese, osmium, iridium and ruthenium.

* * * * *